(12) United States Patent
Kang

(10) Patent No.: US 12,179,043 B2
(45) Date of Patent: Dec. 31, 2024

(54) HANDPIECE FOR NON-FOCUSED ULTRASOUND TREATMENT

(71) Applicant: SHENB Co., Ltd., Seoul (KR)

(72) Inventor: Sun Young Kang, Seoul (KR)

(73) Assignee: SHENB Co., Ltd., Seoul (KR)

( * ) Notice: Subject to any disclaimer, the term of this patent is extended or adjusted under 35 U.S.C. 154(b) by 0 days.

(21) Appl. No.: 18/435,456

(22) Filed: Feb. 7, 2024

(65) Prior Publication Data

US 2024/0350834 A1   Oct. 24, 2024

(30) Foreign Application Priority Data

Apr. 24, 2023   (KR) .................. 10-2023-0053448

(51) Int. Cl.
*A61N 7/00* (2006.01)
*A61N 1/36* (2006.01)

(52) U.S. Cl.
CPC ........... *A61N 7/00* (2013.01); *A61N 1/36021* (2013.01); *A61N 1/36034* (2017.08)

(58) Field of Classification Search
CPC ... A61N 7/00; A61N 1/36021; A61N 1/36034
See application file for complete search history.

(56) References Cited

U.S. PATENT DOCUMENTS 4,140,130 A * 2/1979 Storm, III ............ A61N 1/403
                                                                 219/770
4,989,605 A * 2/1991 Rossen ............ A61N 1/36021
                                                                 607/46
6,605,080 B1 * 8/2003 Altshuler ............ A61B 18/203
                                                                 606/89

(Continued)

FOREIGN PATENT DOCUMENTS

KR           10-1671007 B1      10/2016
KR       10-2017-0095550 A       8/2017

(Continued)

OTHER PUBLICATIONS

Korean Office Action issued on Jul. 2, 2023 in corresponding Korean Patent Application No. 10-2023-0053448. (2 pages in English and 5 pages in Korean).

(Continued)

*Primary Examiner* — Oommen Jacob
(74) *Attorney, Agent, or Firm* — NSIP Law

(57) ABSTRACT

The present disclosure relates to a handpiece for non-focused ultrasound treatment, comprising: a housing; and a cartridge detachably mounted on the housing; wherein the cartridge includes: an ultrasound generator having a transducer; a skin cooling unit; and an EMS skin stimulation unit that provides electrical stimulation to the skin of the person; the skin cooling unit includes: a cooling case; and a thermoelectric element for absorbing heat from the cooling case, the cooling case has an opening through which ultrasound waves generated by the transducer pass, a contact surface is formed around the opening, and the contact surface is in contact with the skin of the person to absorb heat from the skin of the person, and the contact surface forms a cooling wall under the skin of the person around ultrasound waves transferred from the transducer to the skin of the person.

5 Claims, 6 Drawing Sheets

(56) References Cited

U.S. PATENT DOCUMENTS

| | | | | |
|---|---|---|---|---|
| 8,523,791 | B2* | 9/2013 | Castel | A61F 7/00 601/46 |
| 8,932,238 | B2* | 1/2015 | Wing | A61B 8/546 601/2 |
| 2008/0146970 | A1* | 6/2008 | Litman | A61N 7/02 601/2 |
| 2011/0072970 | A1* | 3/2011 | Slobodzian | A61N 7/02 96/197 |
| 2011/0077556 | A1* | 3/2011 | Bockenstedt | A61N 7/02 601/2 |
| 2011/0077557 | A1* | 3/2011 | Wing | A61B 8/546 601/2 |
| 2014/0257108 | A1* | 9/2014 | Morgan | A61N 7/00 600/459 |
| 2018/0154185 | A1* | 6/2018 | Kim | A61N 7/00 |
| 2019/0282834 | A1* | 9/2019 | Zawada | A61B 90/361 |
| 2020/0060571 | A1* | 2/2020 | Dauguet | A61B 5/369 |
| 2020/0086145 | A1* | 3/2020 | Yoo | A61B 90/03 |
| 2021/0393992 | A1* | 12/2021 | Ji | A61N 1/08 |

FOREIGN PATENT DOCUMENTS

| | | |
|---|---|---|
| KR | 10-2022-0002932 A | 1/2022 |
| KR | 20-2022-0000119 A | 1/2022 |
| KR | 10-2604073 B1 | 11/2023 |

OTHER PUBLICATIONS

Korean Decision to Grant a Patent issued on Nov. 10, 2023 in corresponding Korean Patent Application No. 10-2023-0053448. (2 pages in English and 2 pages in Korean.
International search report issued on May 28, 2024, in counterpart International Patent Application No. PCT/KR2024/002101 (3 pages).

* cited by examiner

HANDPIECE FOR NON-FOCUSED ULTRASOUND TREATMENT

CROSS-REFERENCE TO RELATED APPLICATIONS

This application claims priority to Korean Patent Application No. 10-2023-0053448, filed on Apr. 24, 2023, the entire contents of which are incorporated herein by reference.

TECHNICAL FIELD

The present disclosure relates to a handpiece for non-focused ultrasound treatment, and, more specifically, to a handpiece for non-focused ultrasound treatment that generates non-focused ultrasound waves for skin treatment such as procedure for cosmetic purpose.

BACKGROUND

Ultrasound treatment includes High Intensity Focused Ultrasound (HIFU) which focuses and radiates ultrasound waves with a high intensity over 1,000 $W/cm^2$, Low Intensity Focused Ultrasound (LIFU) which focuses and radiates ultrasound waves stronger than those of heat treatment but weaker than those of HIFU, and Low Intensity Pulsed Ultrasound (LIPUS) which radiates non-focused ultrasound waves weaker than those of HIFU.

Non-focused ultrasound waves with an intensity of 5 $W/cm^2$ to 60 $W/cm^2$ are used for skin lifting to cause necrosis by heating subcutaneous tissue, or for sports medicine and musculoskeletal treatment to reduce joint stiffness and muscle spasms and to regenerate cartilage cells.

Compared to treatment using a laser, an IPL, RF, a fractional laser, an LED, etc., treatment using non-focused ultrasound waves has the advantage of less trauma and pain and excellent skin regeneration effects.

Recently, as interest in appearance and skin care increases, interest treatment using non-focused ultrasound waves has been increasing.

However, a person being treated may feel pain or the person's skin may swell since treatment by non-focused ultrasound energy raises the temperature of subcutaneous tissue. Recently, there has been the increasing interest in a handpiece for non-focused ultrasound treatment that is capable of effectively managing the pain and swelling.

In addition, in order to receive treatment by non-focused ultrasound energy, a person to be treated need to visit an institution such as a hospital, causing cost and time.

PRIOR ART DOCUMENT

Patent Document (Patent Document 0001) Korean Laid-open Patent Publication No. 10-2017-0095550 (Aug. 23, 2017)

SUMMARY

The present disclosure provides a handpiece for non-focused ultrasound treatment that may be used by the person being treatment by himself/herself and is capable of effectively relieving pain and swelling in the person's skin.

A handpiece for non-focused ultrasound treatment according to the present disclosure may include a housing and a cartridge detachably mounted on the housing, and the cartridge may include an ultrasound generator having a transducer.

The cartridge may further include a skin cooling unit that cools skin of a person being treated, and an electrical muscle stimulation (EMS) skin stimulation unit that is disposed adjacent to the skin cooling unit and provides electrical stimulation to the skin of the person being treated.

The skin cooling unit may include a cooling case in which an opening through which ultrasound waves generated by the transducer pass is formed, and a contact surface that is in contact with the skin of a person being treated to absorb heat from the skin of the person is formed around the opening of the cooling case. In addition, the skin cooling unit may include a thermoelectric element that absorbs heat from the cooling case to cool the cooling case.

The contact surface may cool subcutaneous layer of the person being treated and prevent heat from being transferred from skin in a treatment area to adjacent skin.

The thermoelectric element may cool the cooling case to a temperature of 0° C. to 15° C.

The EMS skin stimulation unit may include an EMS pad that provides electrical stimulation for relieving pain to the skin of the person being treated, and an EMS control module that controls a current transmitted from the EMS pad to the skin.

The EMS control module may control the EMS pad to apply a microcurrent with an intensity of 1 mA to 100 mA and a frequency of 0 KHz to 10 KHz to the skin of the person being treated.

The present disclosure provides a handpiece for non-focused ultrasound treatment that may be used by the person being treatment by himself/herself and is capable of effectively relieving pain and swelling in the person's skin.

DETAILED DESCRIPTION

Figure 1:
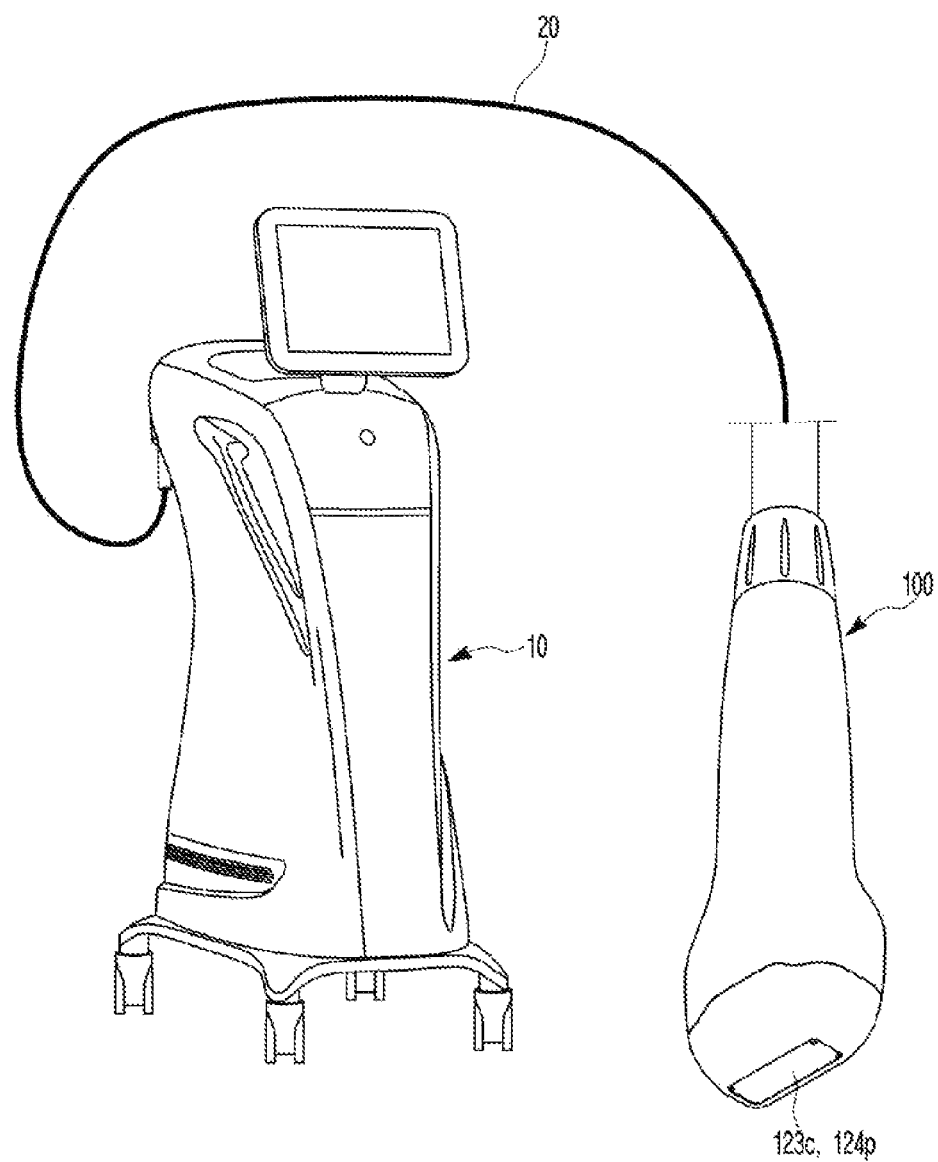
FIG. 1 is a perspective view of a handpiece for non-focused ultrasound treatment, which is connected to a main controller, according to an embodiment of the present disclosure.

Hereinafter, some embodiments of the present disclosure will be described in detail with reference to the illustrative drawings. It should be noted that, when reference numerals were assigned to components in each drawing, the same reference numerals were assigned to the same components as much as possible even when they were shown in different drawings.

In addition, when the embodiments of the present disclosure are described, detailed descriptions of well-known related features or functions will not be provided when it is determined that they hinder understanding of the embodiments of the present disclosure.

Furthermore, when the components in the embodiments of the present disclosure are described, terms such as first, second, A, B, (a), and (b) may be used. Those terms are only intended to distinguish components from other components, and the essence, order, etc. of the components are not limited by the terms.

Figure 2A:
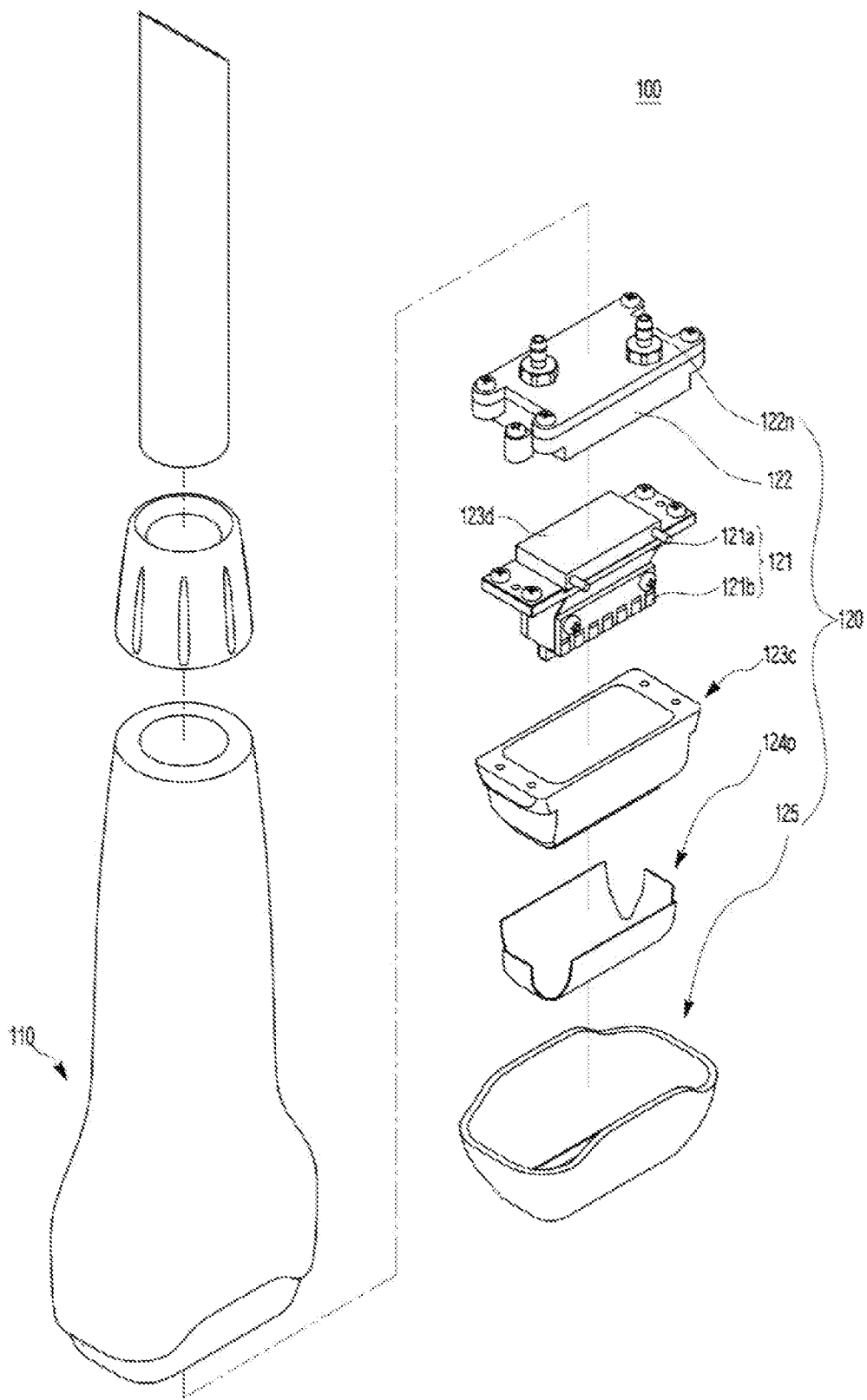
FIGS. 2A, 2B, and 3 are views for illustrating components in the handpiece for non-focused ultrasound treatment in FIG. 1.
Figure 2B:
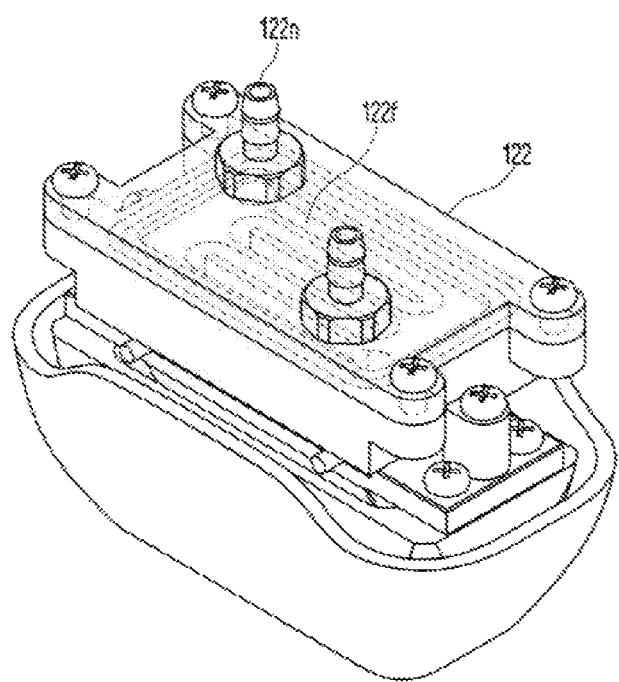
Figure 3:
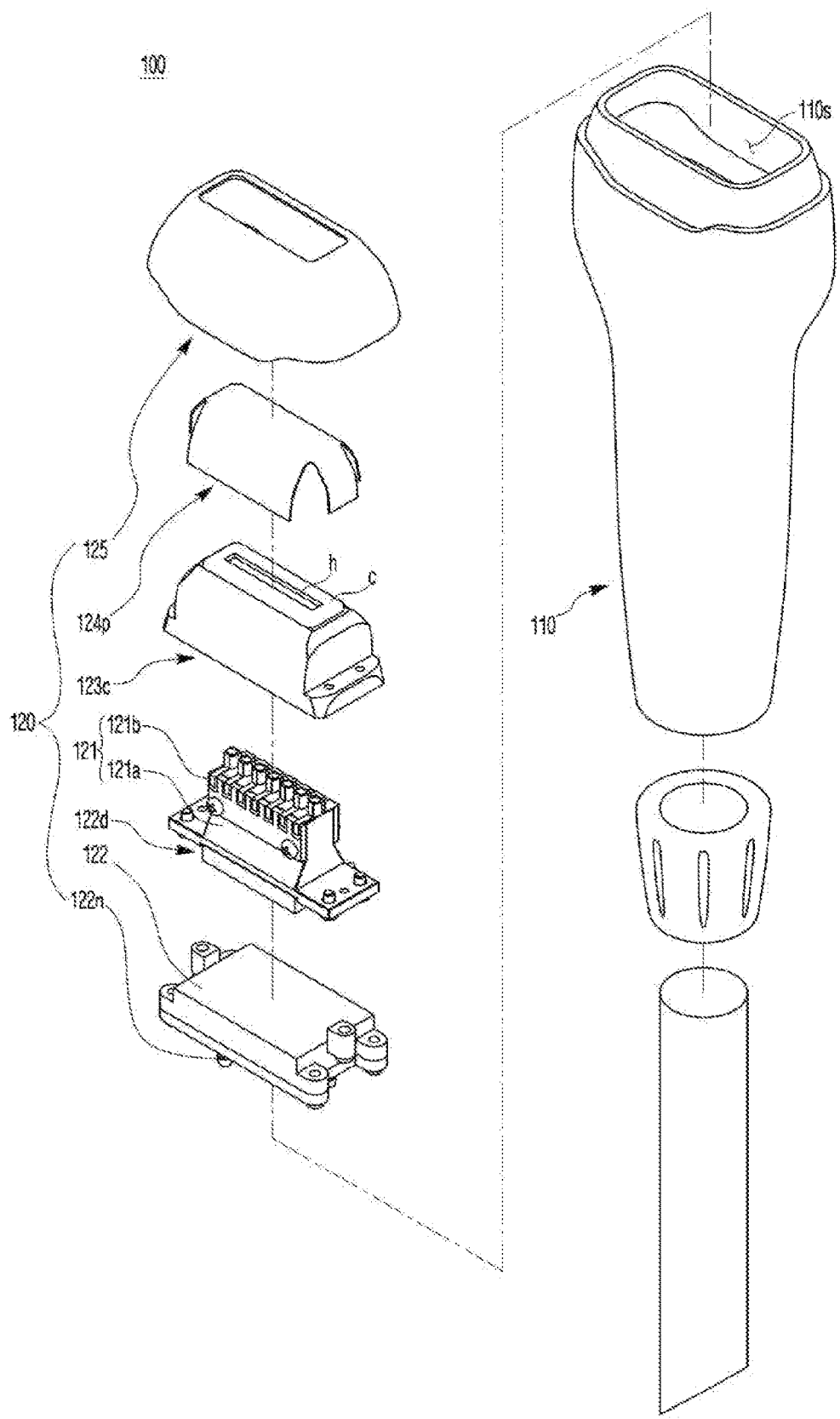
Figure 4:
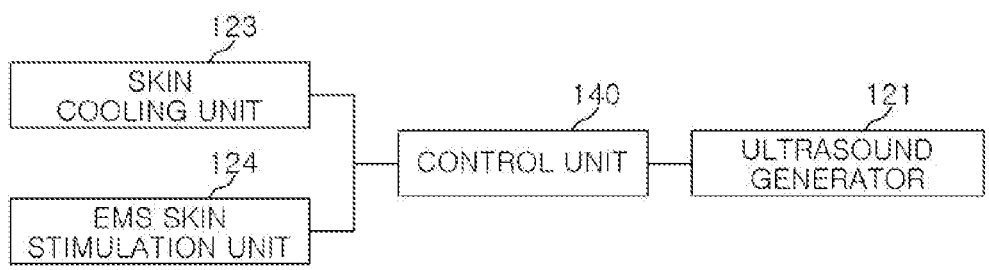
FIG. 4 is a block diagram of a portion of the handpiece for non-focused ultrasound treatment in FIG. 1.
Figure 5A:
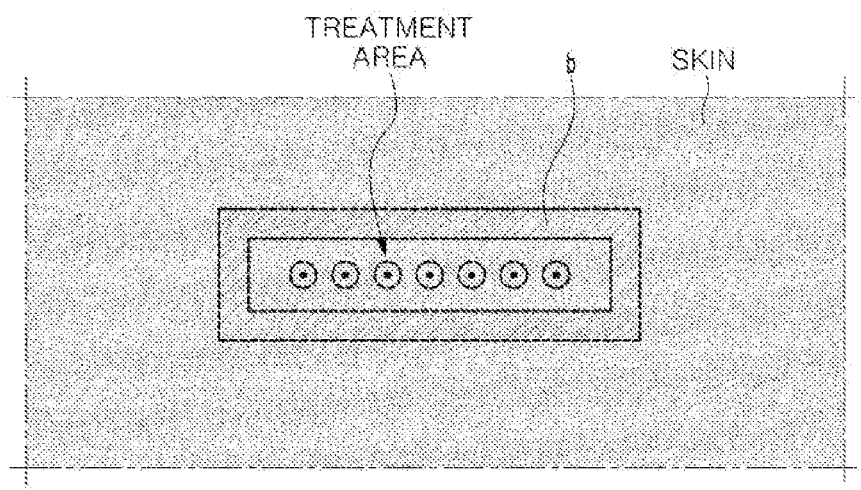
FIGS. 5A and 5B are views for illustrating the skin cooling effect of a cooling case of the handpiece for non-focused ultrasound treatment in FIG. 1.
Figure 5B:
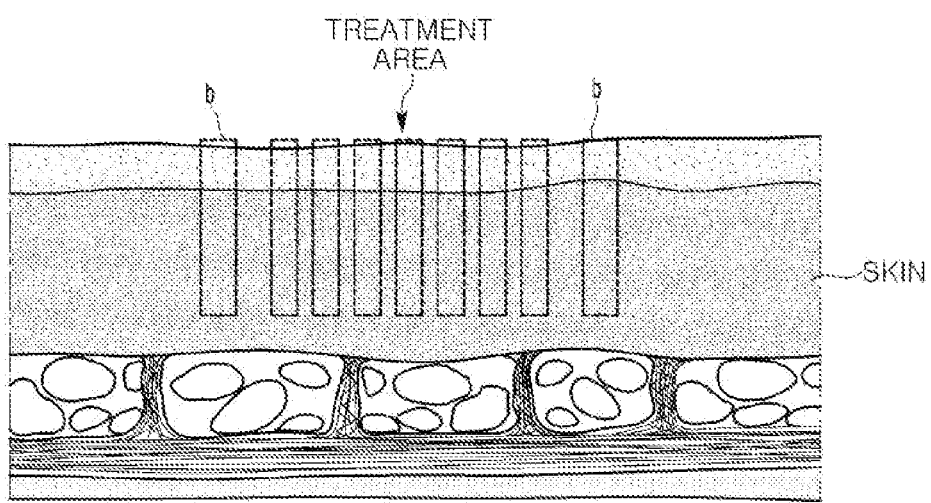

FIG. 1 is a perspective view of a handpiece for non-focused ultrasound treatment, which is connected to a main controller, according to an embodiment of the present disclosure, FIGS. 2A, 2B, and 3 are views for illustrating components in the handpiece for non-focused ultrasound treatment in FIG. 1, FIG. 4 is a block diagram of a portion of the handpiece for non-focused ultrasound treatment in FIG. 1, and FIGS. 5A and 5B are views for illustrating the skin cooling effect of a cooling case of the handpiece for non-focused ultrasound treatment in FIG. 1.

Referring to FIGS. 1 to 5B, a handpiece 100 for non-focused ultrasound treatment according to the present disclosure may be connected to a main controller 10 through a cable 20.

The main controller 10 may include a display, a CPU, a power supply, etc., and provide power and control signals to the handpiece 100 for non-focused ultrasound treatment through the cable 20.

In addition, the main controller 10 may include a pump, a heat exchanger, etc., and circulate coolant through the cable 20 to the handpiece 100 for non-focused ultrasound treatment.

The handpiece 100 for non-focused ultrasound treatment may be operated by power, control signals, etc. provided by the main controller 10.

Specifically, the handpiece 100 for non-focused ultrasound treatment may heat subcutaneous tissue with non-focused ultrasound waves in the range of 5 W/cm$^2$ to 60 W/cm$^2$ to cause necrosis, and may be used for skin care or plastic surgery such as skin lifting and wrinkle care.

The handpiece 100 for non-focused ultrasound treatment may include a housing 110 and a cartridge 120.

A mounting portion 110s may be formed at a lower part of the housing 110, and the cartridge 120 may be detachably mounted on the lower part of the housing 110.

The housing 110 may be equipped with an electrical component(s) connected to the cable 20.

In addition, the housing 110 may include a tube for supplying coolant to the cartridge 120 or recovering coolant from the cartridge 120.

Specifically, the tube included in the housing 110 may be connected to each of the cable 20 and a water block 122 of the cartridge 120 to circulate coolant in the water block 122.

The cartridge 120 may include an ultrasound generator 121, the water block 122, a skin cooling unit 123, and an electrical muscle stimulation (EMS) skin stimulation unit 124.

The ultrasound generator 121 may be located above the skin cooling unit 123 and generate ultrasound waves.

The ultrasound generator 121 may include a cooling block 121a and a transducer 121b.

The upper surface of the cooling block 121a may be in contact with the water block 122, and the transducer 121b may be fixed to the lower side of the cooling block 121a.

Specifically, the transducer 121b may be formed by attaching ceramic to the lower side of the cooling block 121a with brass and aluminum tape.

The transducer 121b may generate non-focused ultrasound waves in a linear focus shape.

When ultrasound waves are emitted from the transducer 121b, heat generated from the transducer 121b may be transferred to the water block 122 through the cooling block 121a.

That is, the water block 122 may cool the transducer 121b and maintain the temperature of the transducer 121b at an appropriate level.

The ultrasound generator 121 may be disposed below the water block 122, and the cooling water flowing in the water block 122 may cool the ultrasound generator 121 by absorbing heat generated from the transducer 121b of the ultrasound generator 121.

A nipple 122n through which coolant flows in and out may be installed above the water block 122.

The nipple 122n may include two nipples. Specifically, the nipple 122n may include an inlet nipple connected to the tube of the housing 110 and receiving coolant from the housing 110 and an outlet nipple that discharges coolant that has absorbed heat transferred from the cooling block 121a to the water block 122 to the housing 110.

A flow path 122f may be formed within the water block 122 to increase the area for exchanging heat with the water block 122 (see FIG. 2B).

Coolant flowing into the inlet nipple may absorb heat transferred from the cooling block 121a to the water block 122 while passing through the flow path 122f, and then the coolant absorbing heat may be discharged to the outlet nipple.

The skin cooling unit 123 may be in contact with the skin of a person being treated during treatment and rapidly absorb heat from the skin of the person, thereby reducing pain in the skin of the person.

Specifically, when the ultrasound generator 121 emits ultrasound waves, the skin cooling unit 123 may come into contact with the skin of a person being treated and rapidly absorb heat from the skin of the person being treated.

The skin cooling unit 123 may include a cooling case 123c and a thermoelectric element 123d.

An opening h through which ultrasound waves generated by the transducer 121b of the ultrasound generator 121 pass may be formed at the cooling case 123c.

Around the opening h of the cooling case 123c, a contact surface c that is in contact with the skin of a person being treated and absorbs heat from the skin of the person may be formed.

The contact surface c may form a cooling wall b under the skin of the person being treated around ultrasound waves transferred from the transducer 121b to the skin, so as to prevent heat generated in a treatment area on the person's skin from being delivered to adjacent skin of the treatment area (see FIGS. 5A and 5B).

Meanwhile, as shown in FIG. 5B, the cooling wall b may be formed in the subcutaneous layer adjacent to heat generated in the treatment area depending on a cooling temperature, and may also be formed as a cooling wall that does not penetrate deeply into the skin in order to cool only the outer surface of the skin, such as the epidermal layer.

The cooling case 123c may be connected to the thermoelectric element 123d.

The thermoelectric element 123d may be in contact with the cooling case 123c to cool the cooling case 123c by absorbing heat from the cooling case 123c.

Specifically, the upper surface of the cooling block 121a may be in contact with the lower surface of the thermoelectric element 123d, and the upper surface of the cooling case 123c may be in contact with the lower surfaces on both sides of the cooling block 121a.

Therefore, heat from the cooling case 123c may be absorbed into the thermoelectric element 123d through the cooling block 121a.

The thermoelectric element 123d may include a Peltier module made of $Bi_2TeO_3$, and may convert heat energy absorbed by the cooling case 123c into electrical energy.

The thermoelectric element 123d may cool the cooling case to 123c to 0° C. to 15° C. The cooling case 123c may absorb heat from the skin heated by ultrasound waves emitted from the ultrasound generator 121, thereby reducing pain in the skin of a person being treated.

Meanwhile, the water block 122 described above may absorb heat from the thermoelectric element 123d through a surface in close contact with the thermoelectric element 123d and discharge heat to the outside. The water block 122 and one surface of the thermoelectric element 123d are tightly adhered and fully combined, and it is necessary to prevent heat absorbed by the water block 122 from being conducted to the cooling block 121a or the cooling case 123c.

Therefore, the water block 122 and the cooling block 121a may be placed on the upper and lower sides of the thermoelectric element 123d, respectively, and both upper sides of the water block 122 and the thermoelectric element 123d may be coupled to the cooling block 121a by separate fastening members such as bolts (not shown in the drawings), so that the water block 122, the thermoelectric element 123d, and the cooling block 121a may be overlapped and fixed to each other. Here, the fastening member may be made of a material with low thermal conductivity, such as plastic, to prevent heat delivered to the water block 122 from moving back to the cooling case 123c, thereby avoiding a reduction in cooling efficiency.

Heat from the transducer 121b may be absorbed into the thermoelectric element 123d through the cooling block 121a. The internal space of the cooling case 123c may be filled with distilled water, which is a medium for transmitting ultrasound waves generated by the ultrasound generator 121.

The ultrasound generator 121 may be mounted on the cooling case 123c such that the transducer 121b may be located in the internal space.

Specifically, the cooling case 123c may be filled with distilled water, and may be mounted on the cooling block 121a such that the transducer 121b may be inserted into the cooling case.

Accordingly, ultrasound waves generated by the transducer 121b may be transmitted to the skin of a person being treated through the distilled water in the cooling case 123c.

The EMS skin stimulation unit 124 may stimulate the skin of a person being treated by flowing a micro-current to the skin of the person, thereby reducing pain in the skin of the person.

Cooling of the skin of a person being treated by the skin cooling unit 123 and stimulating of the skin by the EMS skin stimulation unit 124 may be performed independently or simultaneously.

The EMS skin stimulation unit 124 may include an EMS pad 124p and an EMS control module (not shown).

The EMS control module (not shown) may control current delivered from the EMS pad 124p to the skin. Accordingly, the EMS pad 124p may provide electrical stimulation for relieving pain to the skin of a person being treated.

The cooling case 123c and the EMS pad 124p may be formed integrally, or the EMS pad 124p may be made to cover a predetermined portion of the cooling case 123c.

The EMS control module (not shown) may control the EMS pad 124p to apply a microcurrent with an intensity of 1 mA to 100 mA and a frequency of 0 KHz to 10 KHz to the skin of a person being treated.

The handpiece 100 for non-focused ultrasound treatment may further include a control unit 140.

The control unit 140 may be connected to each of the ultrasound generator 121, the skin cooling unit 123, and the EMS skin stimulation unit 124.

Specifically, the control unit 140 may be connected to each of the transducer 121b of the ultrasound generator 121, the thermoelectric element 123d of the skin cooling unit 123, and the EMS control module (not shown) of the EMS skin stimulation unit 124, and may transmit control signals to the transducer 121b, the thermoelectric element 123d, and the EMS control module (not shown).

Example 1_Control of Skin Cooling Temperature and Skin Irritation

While a person being treated is receiving a treatment using non-focused ultrasound waves, the temperature of the cooling case 123c is controlled to 3° C. to 5° C., and the intensity and the frequency of the microcurrent of the EMS pad 124p are controlled to 80 mA to 100 mA and 1 kHz to 10 KHz, respectively.

Comparative Example 1_Skin Cooling Temperature

While a person being treated is receiving a treatment using non-focused ultrasound waves, the temperature of the cooling case 123c is controlled to 3° C. to 5° C., and the intensity of the microcurrent of the EMS pad 124p is controlled to 0 mA.

Experimental Example 1_Experiment on Pain of Persons being Treated

Twenty female persons being treated in their 40s weighing between 48 kg and 73 kg were the subjects of the experiment, and the subjects were randomly divided into Group A and Group B, each having 10 subjects. In the case of Group A, an increase or decrease in pain was observed while a treatment using non-focused ultrasound waves was performed on wrinkles around the right eye of the persons being treated under the conditions of Comparative Example 1 after a treatment using non-focused ultrasound waves had been performed on wrinkles around the left eye of the persons being treated under the conditions of Example 1. In the case of Group B, an increase or decrease in pain was observed while a treatment using non-focused ultrasound waves was performed on wrinkles around the right eye of the persons being treated under the conditions of Example 1 after a treatment using non-focused ultrasound waves had been performed on wrinkles around the left eye of the persons being treated under the conditions of Comparative Example 1.

When the treatment under the conditions of Comparative Example 1 began after the treatment under the conditions of Example 1, all the subjects in Group A felt an increase in pain, and Table 1 below shows how much pain increased in the subjects in Group A.

In Table 1 below, a score of 5 was given when subjects felt a very significant increase in pain, 4 was given when subjects felt a significant increase in pain, 3 was given when subjects felt a moderate increase in pain, 2 was given when subjects felt a slight increase in pain, and 1 was given when subjects did not feel an increase in pain.

TABLE 1

| | Subject | | | | | | | | | |
|---|---|---|---|---|---|---|---|---|---|---|
| | 1 | 2 | 3 | 4 | 5 | 6 | 7 | 8 | 9 | 10 |
| Increase in Pain | 3 | 4 | 3 | 4 | 5 | 4 | 4 | 3 | 3 | 4 |

All the subjects in Group A experienced a significant increase in pain when the treatment under the conditions of Comparative Example 1 began after the treatment under the conditions of Example 1. All the subjects in Group B felt pain relief when the treatment under the conditions of Example 1 began after the treatment under the conditions of Comparative Example 1. Table 2 below shows how much pain relief the subjects in Group B felt.

In Table 2 below, a score of A was given when subjects felt very great pain relief, B was given when subjects felt great pain relief, C was given when subjects felt moderate pain relief, D was given when subjects felt slight pain relief, and F was given when subjects did not feel pain relief.

TABLE 2

| | Subject | | | | | | | | | |
|---|---|---|---|---|---|---|---|---|---|---|
| | 1 | 2 | 3 | 4 | 5 | 6 | 7 | 8 | 9 | 10 |
| Decrease in Pain | B | B | A | B | A | A | B | A | A | A |

All the subjects in Group B experienced significant pain relief when the treatment under the conditions of Example 1 began after the treatment under the conditions of Comparative Example 1. In other words, it was confirmed that pain in the skin of a person receiving the treatment was greatly alleviated when the treatment using non-focused ultrasound waves was performed according to Example 1 of the present disclosure.

Experimental Example 2 Experiment on Swelling of Persons being Treated

Twenty female persons being treated in their 40s weighing between 48 kg and 73 kg were the subjects of the experiment, and the subjects were randomly divided into Group A and Group B, each having 10 subjects. In the case of Group A, it was observed how much swelling occurred while a treatment using non-focused ultrasound waves was performed on wrinkles around the left eye of the persons being treated under the conditions of Example 1 after a treatment using non-focused ultrasound waves without skin cooling and an EMS current stimulation had been performed on wrinkles around the right eye of the persons being treated. In the case of Group B, it was observed how much swelling occurred while a treatment using non-focused ultrasound waves was performed on wrinkles around the left eye of the persons being treated under the conditions of Comparative Example 1 after a treatment using non-focused ultrasound waves without skin cooling and an EMS current stimulation had been performed on wrinkles around the right eye of the persons being treated.

It was visually confirmed that less swelling had occurred around the left eye of all the subjects in Group A than around the right eye.

Table 3 below shows the scores given for swelling around the left eye when a score of 5 was given for swelling around the right eye. When the degree of swelling around the left eye was 100% to 80% of the swelling around the right eye, a score of 5 was given; when the degree of swelling around the left eye was 79% to 60% of the swelling around the right eye, a score of 4 was given; when the degree of swelling around the left eye was 59% to 40% of the swelling around the right eye, a score of 3 was given; when the degree of swelling around the left eye was 39% to 20% of the swelling around the right eye, a score of 2 was given; and when the degree of swelling around the left eye was 19% to 0% of the swelling around the right eye, a score of 1 was given.

TABLE 3

| | Subject | | | | | | | | | |
|---|---|---|---|---|---|---|---|---|---|---|
| | 1 | 2 | 3 | 4 | 5 | 6 | 7 | 8 | 9 | 10 |
| Degree of Swelling | 2 | 2 | 1 | 1 | 1 | 1 | 1 | 2 | 1 | 1 |

It was confirmed that the treatment using non-focused ultrasound waves according to Example 1 was highly effective in reducing swelling. It was also visually confirmed that less swelling had occurred around the left eye of all the subjects in Group B than around the right eye. Table 4 below shows the scores given for swelling around the left eye when a score of 5 was given for swelling around the right eye. When the degree of swelling around the left eye was 100% to 80% of the swelling around the right eye, a score of 5 was given; when the degree of swelling around the left eye was 79% to 60% of the swelling around the right eye, a score of 4 was given; when the degree of swelling around the left eye was 59% to 40% of the swelling around the right eye, a score of 3 was given; when the degree of swelling around the left eye was 39% to 20% of the swelling around the right eye, a score of 2 was given; and when the degree of swelling around the left eye was 19% to 0% of the swelling around the right eye, a score of 1 was given.

TABLE 4

| | Subject | | | | | | | | | |
|---|---|---|---|---|---|---|---|---|---|---|
| | 1 | 2 | 3 | 4 | 5 | 6 | 7 | 8 | 9 | 10 |
| Degree of Swelling | 2 | 2 | 2 | 3 | 3 | 3 | 4 | 3 | 3 | 2 |

The treatment using non-focused ultrasound waves according to Comparative Example 1 was effective in reducing swelling, but was not more effective than the treatment using non-focused ultrasound waves according to Example 1.

All components in the embodiments of the present disclosure have been described as being combined or operating in combination, but the present disclosure is not necessarily limited to the embodiments. That is, one or more of the components may be selectively combined to operate within the scope of the purpose of the present disclosure.

In addition, unless defined otherwise, all terms used herein, including technical or scientific terms, have a meaning consistent with the meaning commonly understood by a person having ordinary skills in the technical field to which the present disclosure belongs. Commonly used terms such as terms defined in dictionaries should be interpreted as having meanings consistent with the meanings in the context of the related technology, and should not be construed in an ideal or overly formal sense unless explicitly defined in the present disclosure.

The description above is only an exemplary description of the technology of the present disclosure, and various modifications and changes within the scope of the essential characteristics of the present disclosure will be possible to a person having ordinary skill in the technical field to which the present disclosure belongs. Therefore, the embodiments disclosed in the present disclosure are not intended to limit the technology of the present disclosure, but to explain them, and the scope of the technology of the present disclosure is not limited by the embodiments. The scope of the present disclosure should be determined based on the following claims, and all technologies within the scope equivalent thereto should be deemed to be included in the scope of the present disclosure.

The invention claimed is:

1. A handpiece for non-focused ultrasound treatment, comprising:
 a housing; and
 a cartridge detachably mounted on the housing,
 wherein the cartridge includes:
 an ultrasound generator having a transducer and a cooling block, the transducer being fixed to a lower side of the cooling block;
 a skin cooler for cooling skin of a person being treated; and
 an electrical muscle stimulation (EMS) skin stimulator disposed adjacent to the skin cooler, the EMS skin stimulator providing electrical stimulation to the skin of the person,
 the skin cooler includes:
 a cooling case; and
 a thermoelectric element connected to the cooling case to absorb heat from the cooling case,
 wherein the cooling case has an opening through which ultrasound waves generated by the transducer pass,
 a contact surface is formed around the opening of the cooling case, and the contact surface is in contact with the skin of the person to absorb heat from the skin of the person, and
 the contact surface forms a cooling wall under the skin of the person around ultrasound waves transferred from the transducer to the skin of the person,
 wherein the cartridge further includes:
 a water block for discharging heat from the thermoelectric element,
 wherein the water block is fixed to an upper side of the thermoelectric element, and the cooling block is fixed to a lower side of the thermoelectric element, and
 heat generated by the transducer is directly absorbed by the thermoelectric element through the cooling block and then transferred to the water block, and
 wherein when the cartridge is replaced, the cartridge including the transducer, the cooling block, the thermoelectric element, and the water block are detached from the housing.

2. The handpiece of claim 1, wherein the contact surface cools subcutaneous layer of the person and prevents heat from being transferred from skin in a treatment area to adjacent skin.

3. The handpiece of claim 1, wherein the thermoelectric element cools the cooling case to a temperature of 0° C. to 15° C.

4. The handpiece of claim 1, wherein the EMS skin stimulator includes:
 an EMS pad that provides electrical stimulation for relieving pain to the skin of the person; and
 an EMS control module that controls a current transmitted from the EMS pad to the skin.

5. The handpiece of claim 4, wherein the EMS control module controls the EMS pad to apply a microcurrent with an intensity of 1 mA to 100 mA and a frequency of 0 kHz to 10 kHz to the skin of the person.

* * * * *